United States Patent
Pakes et al.

[19]

[11] Patent Number: 6,119,509
[45] Date of Patent: Sep. 19, 2000

[54] ASSESSING THE FUNCTIONAL PROPERTIES OF DRIED MILK PRODUCTS

[75] Inventors: Natalie Elizabeth Pakes; Mark Leonard Bason, both of New South Wales, Australia

[73] Assignee: Newport Scientific Pty. Limited, New South Wales, Australia

[21] Appl. No.: 09/216,940

[22] Filed: Dec. 21, 1998

[30] Foreign Application Priority Data

Dec. 23, 1997 [AU] Australia ................... PP1074

[51] Int. Cl.[7] ............... G01N 11/00; A23C 9/16
[52] U.S. Cl. .......................... 73/54.02; 426/588
[58] Field of Search ............... 73/54.02, 54.01; 426/570, 573, 609, 588, 583, 582

[56] References Cited

U.S. PATENT DOCUMENTS

| | | | |
|---|---|---|---|
| 3,985,902 | 10/1976 | Coste | 426/582 |
| 4,496,604 | 1/1985 | Otsubo | 426/588 |
| 4,879,897 | 11/1989 | Booth et al. | |
| 4,884,894 | 12/1989 | Hahimoto et al. | 366/338 |
| 4,938,976 | 7/1990 | Shemer | |

FOREIGN PATENT DOCUMENTS

| | | |
|---|---|---|
| 0674873 | 7/1952 | United Kingdom |
| 1422830 | 1/1976 | United Kingdom |

OTHER PUBLICATIONS

Abstract of Japanese patent JP 61162127 A, WPI Accession No. 86–230352/198635.

Primary Examiner—Daniel S. Larkin
Assistant Examiner—Jay L. Politzer
Attorney, Agent, or Firm—Smith Gambrell & Russell, LLP

[57] ABSTRACT

A method for assessing the properties of dried milk products and hence suitability for use in various processes is described, including the steps of solubilizing a sample of a dried milk product, stirring the sample mixture and assessing the viscosity of the solution. The solvent can be water or a dilute acid buffered to approximately pH 6.5 and the sample mixture heated to at least 50° C. to solubilize the proteins in the dried milk product while the viscosity is measured.

13 Claims, 3 Drawing Sheets

ASSESSING THE FUNCTIONAL PROPERTIES OF DRIED MILK PRODUCTS

BACKGROUND OF THE INVENTION

This invention relates to a method for assessing the functional properties of dried milk products, which products are used in the production of various foods such as infant formulas, cheese, yoghurt or chocolate.

DESCRIPTION OF THE PRIOR ART

Milk is a complex fluid the major components of which are water, fat, lactose, caseins, whey proteins and minerals in amounts varying with the milk of different animal species.

Caseins make up about 80% of bovine milk proteins, the remaining proteins being classified as whey proteins. Caseins (of which there are five fractions, ($\alpha_{S1}$-, $\alpha_{S2}$-, $\beta$-, $\gamma$-, $\kappa$-) and whey proteins differ from each other in their physical and chemical characteristics. Caseins become insoluble at pH 4.6 and below whereas whey proteins are soluble at these pH levels. Caseins exist in milk as particles called micelles which are made up of calcium phosphate and casein complexes. All of the casein fractions except $\kappa$-casein are precipitated by calcium. $\kappa$-casein stabilises the micelles by surface binding. During cheese making, the stabilising $\kappa$-casein is cleaved by the enzyme rennin, destabilising the micelles and subsequently forming curds. Whey is the watery liquid which remains after the curd is formed in the manufacture of cheese and fermented or acidified dairy products such as yoghurt.

By removing water from milk, low-fat milk, skim milk and liquid whey, and by further processing, a series of dried dairy ingredients is obtained, including skim milk powder, skim milk isolate, whey powder, whey protein concentrate, whey isolate, casein, and caseinates. These are widely used in the formulation of a number of food products to provide the desirable attributes of nutrition, water-binding, fat-holding, emulsification, viscosity, gelation and foaming, as well as texture and flavour.

The functional properties of these dried dairy ingredients and their performance in a particular food system are related both to their chemical compositions, and to the specific processing conditions, such as heating and shear, to which they have been subjected during their preparation and drying. Dried milk products containing whey proteins are particularly susceptible to modification by heating during their production, leading to changes in protein "quality".

The amounts of protein in commonly-used dry dairy ingredients are as follows:
  whey protein (WP) (dry) 11–14.5%
  whey protein concentrate (WPC) approximately 70% (range 34–80%)
  whey protein isolate approximately 92%
  skim milk powder (SMP) approximately 30–35%

To form WPC from whey, the minerals and lactose are removed. WPC and WP are used as fat mimetics, gelling agents and nutritional ingredients in foods such as yoghurt, bakery mixes, desserts, chocolate and confections. The water-binding ability, fat-like mouthfeel and gelation property of WPC are particularly useful in the above food products.

It is advantageous in the food processing industry to know beforehand, what type of dairy ingredient is best suited for a particular application and to be able to predict, and test for, what processing conditions would produce a dairy ingredient for a particular application, e.g. an SMP with low viscosity and weak gelling properties, suitable for chocolate-making.

The prior art tests for measuring the properties of dehydrated milk products include hydrophobicity, solubility, foaming capacity and foam stability. Disadvantages of these known methods are that they are difficult and lengthy to conduct so normally are confined to research applications and that they do not predict for which food processing applications a particular dairy ingredient would be most suited.

Apparatus which measure the viscosity of cheese and yoghurt are known, but these test the end-products and are not used as a predictive test on the dairy ingredients used in the manufacture of the cheese or yoghurt.

SUMMARY OF THE INVENTION

The object of the present invention is to overcome the disadvantages of the prior art by providing a more convenient method for assessing the functional properties of dried milk products, the characteristics of which products are dependent on the processing history of the product and affect the suitability of the products for further processing and for different food applications.

In a first form, the invention provides a method for assessing the functional properties of dried milk products, comprising taking a sample of the dried milk product, mixing the sample with a solvent and subjecting the mixture to conditions suitable for the milk proteins in the sample to enter solution, stirring the solution and assessing the viscosity of the solution.

The solution preferably is heated to at least 50° C., most preferably to about 70–90° C., while the viscosity is measured.

Preferred apparatus for carrying out the assay method includes a sample container into which the sample and solvent are placed, heat transfer means for controlled heating of the sample, stirring means positioned within the container and means for analysing and recording the temperature and the viscosity of the solution.

BRIEF DESCRIPTION OF THE DRAWINGS

Further preferred embodiments of the invention now will be described with reference to the accompanying drawings, in which.

DETAILED DESCRIPTION OF THE PREFERRED EMBODIMENTS

Figure 1:
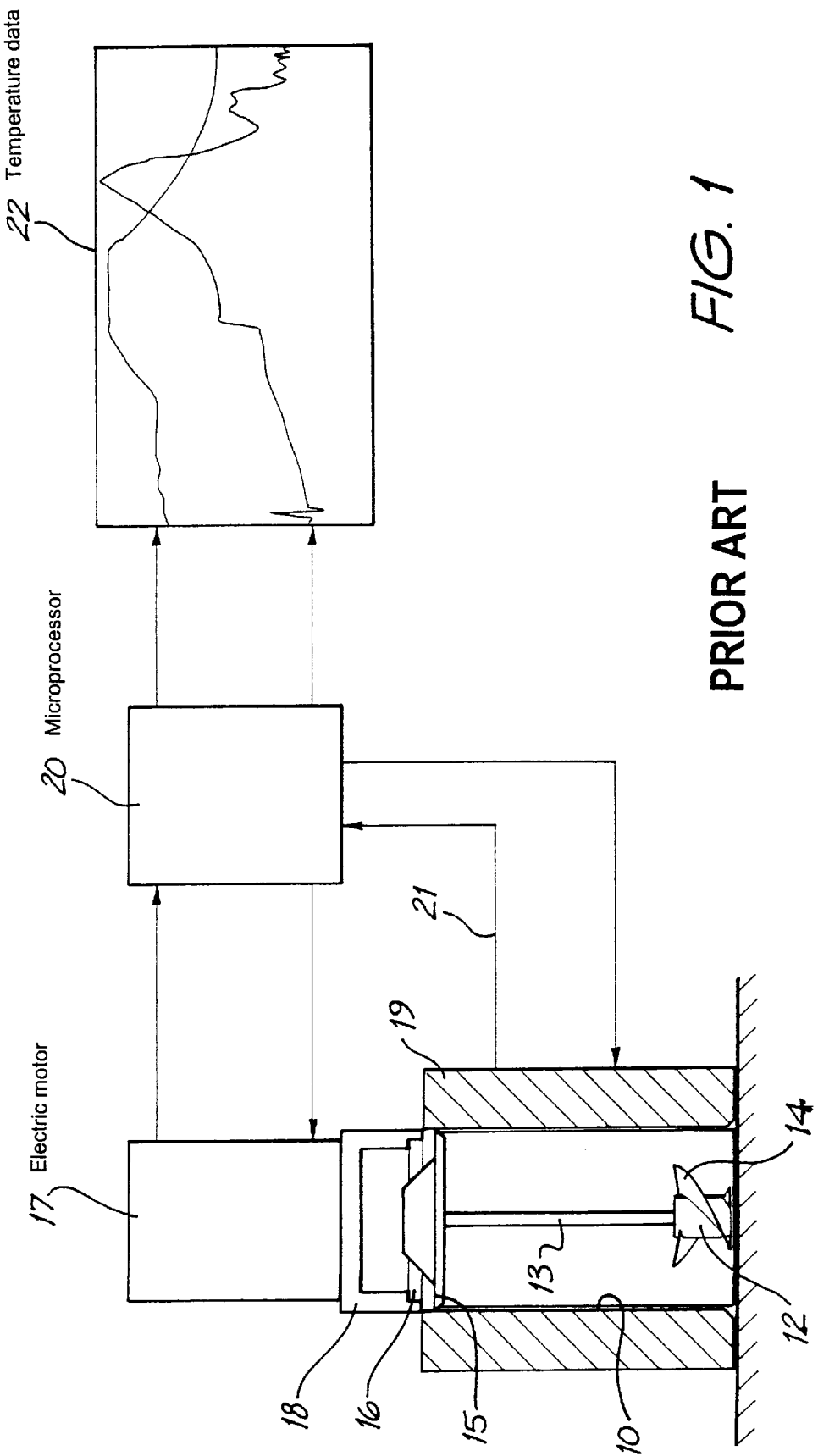
FIG. 1. is a schematic representation of the viscometer apparatus suitable for use in the invention.

A viscometer apparatus suitable for use in preferred embodiments of the invention is the Rapid Visco Analyser (RVA) manufactured by Newport Scientific Pty Ltd of Sydney, Australia. FIG. 1 is a schematic illustration of that apparatus. A more complete description of its construction and operation may be found in U.S. Pat. No. 4,879,897, the contents of which are incorporated herein by reference.

The apparatus of FIG. 1 includes a cylindrical sample canister 10 having a side wall of heat-conductive material such as aluminium and a stirrer 12 including a stem 13 and a paddle 14. At the top of the stirrer 12 there is provided a plate 15 to allow connection with drive coupling 18.

An electric motor 17 and drive coupling 18 arrangement is movable from a position allowing insertion and removal of the canister 10 to the position shown in FIG. 1, in which the motor 17 is positioned directly over the canister 10 and the drive coupling 18 engages the plate 15 to drive rotation of the stirrer 12.

Heating blocks 19 clamp into contact with the side wall of the canister 10 to transfer heat through the canister 10 to its contents. Heating of the blocks 19 is controlled by a microprocessor 20 to create a desired temperature profile over the test cycle.

A temperature sensor (not shown) in the vicinity of the canister 10 provides an input signal to the microprocessor 20 and the temperature data 22 is recorded on computer disc for later analysis and display.

Simultaneously with the commencement of heating, the stirrer 12 is rapidly rotated at approximately 800–1000 rpm for at least 30 seconds, preferably about 1 minute or more. This is important to achieve proper mixing of the sample in the canister 10. The stirrer 12 thereafter is run more slowly, at a known speed in a range of about 100–500 rpm, for assessment of the viscosity by measuring the current required by the motor 17. The viscosity output also is recorded on computer disc for later analysis and display.

In a preferred assay method, a sample of dairy ingredient product is placed in the canister 10. Solvent is added at room temperature and the mixture is agitated to form a slurry. The stirrer 12 is placed in the canister 10, which then is placed in the RVA apparatus as shown in FIG. 1.

The initial rapid stirring of the sample places the milk protein in homogeneous suspension. As the temperature increases, the viscosity of the solution increases. The viscosity characteristics of the solution recorded in this test have been shown to correlate to methods of processing to which the dried milk product sample has been subjected, which processing methods in turn have been shown to impinge on the end-use of the dried milk products. The method of the present invention provides the ability to detect which processing history (high- or low-heat processing) the dried milk products had undergone and therefore gives information about the suitability of the dried milk product for various food applications.

EXAMPLE 1
Whey protein concentrate

Into a canister of an RVA apparatus was placed distilled water and onto the surface of the water was placed an amount of WPC to provide 4.50 g protein in 28.5 g solution. The sample mixture was shaken vigorously for 30 s to form a slurry.

A stirrer was placed into the canister, which was then placed into the RVA apparatus as shown in FIG. 1.

The RVA apparatus commenced heating and initial rapid stirring of the sample mixture at 1000 rpm to place the WPC into homogeneous suspension. The microprocessor controlled gradual heating of the sample mixture ramping up to about 80° C., held at that temperature, and then allowed cooling, over a 20-minute test cycle. Concurrently, the stirrer was run at 320 rpm and the viscosity of the solution calculated from measuring the current.

The test profile was as follows:

| Time | Type | Value |
| --- | --- | --- |
| 00:00:00 | Temp | 50° C. |
| 00:00:00 | Speed | 1000 rpm |
| 00:01:00 | Speed | 320 rpm |
| 00:01:00 | Temp | 50° C. |
| 00:04:30 | Temp | 80° C. |
| 00:09:30 | Temp | 80° C. |
| 00:15:00 | Temp | 30° C. |
| Idle temperature: 50° C. | | |
| End of test: 20 min | | |
| Time between readings: 4s | | |

Figure 2:
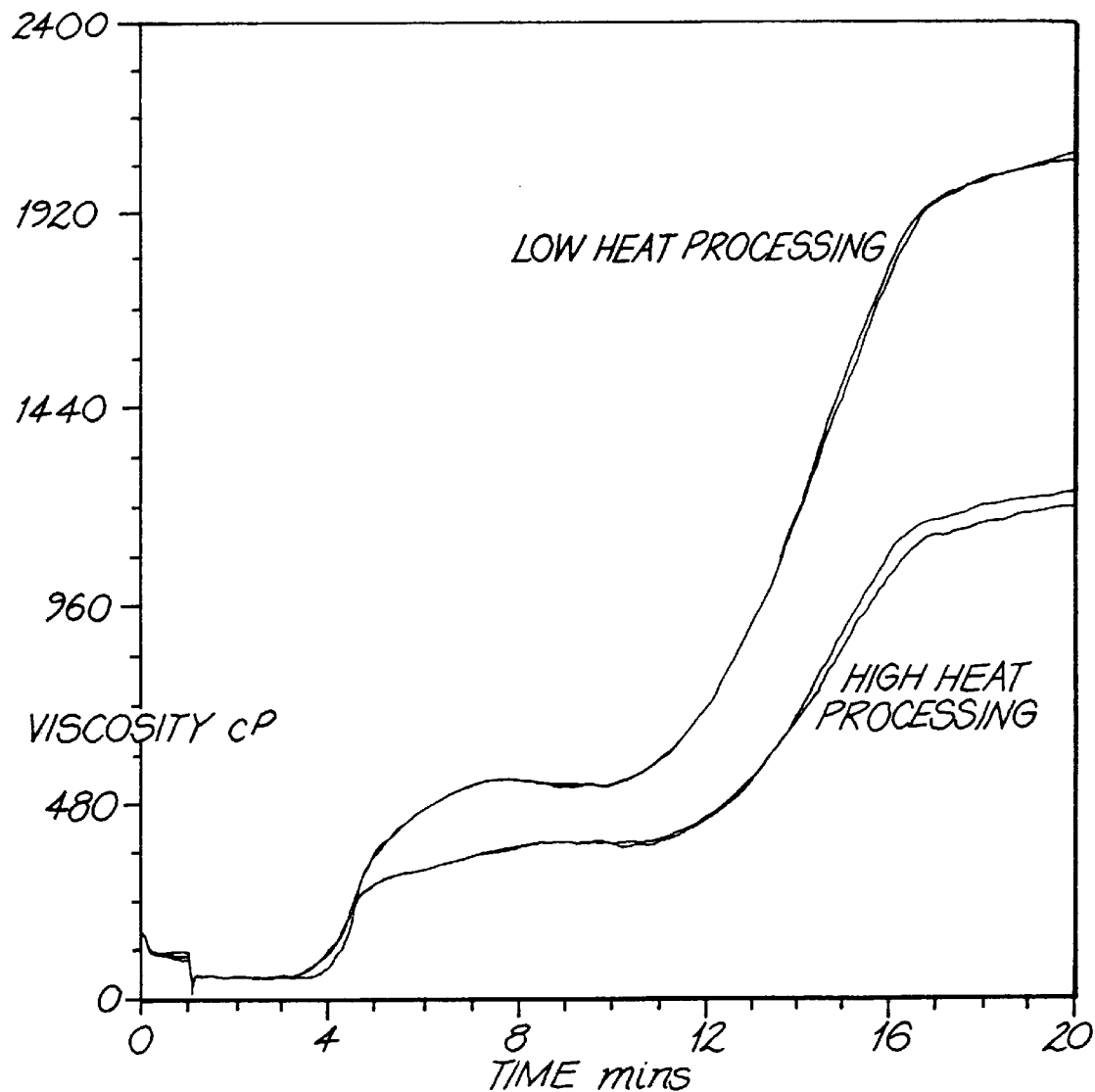
FIG. 2 is a sample result graph in which both temperature and viscosity readings of a whey protein concentrate sample are plotted against time.

FIG. 2 is a copy of the resultant plots of viscosity (left hand axis) against time, for samples of WPC which had undergone high or low heat processing. As the sample mixture was heated to and held at around 80° C., the viscosity of the sample mixture rose and reached a first plateau. The viscosity rose and reached another plateau as the sample mixture was cooled. It is apparent that the test readily distinguishes the different processing histories of the two WPC samples.

The dual lines for viscosity for each WPC type indicate the test results for two different samples from the same source. It can be seen that the results were highly reproducible.

EXAMPLE 2
Skim Milk Powder

Into a canister of an RVA apparatus was placed distilled water and onto the surface of the water was placed an amount of SMP to provide 4.50 g protein, in 28.5 g solution. The sample mixture was shaken vigorously for 30 s to form a slurry.

A stirrer was placed into the canister, which was then placed into the RVA apparatus as shown in FIG. 1.

The RVA apparatus commenced heating and initial rapid stirring of the sample mixture at 1000 rpm to place the SMP into homogeneous suspension. The microprocessor controlled gradual heating of the sample mixture ramping up to about 90° C., held at that temperature, and then allowed cooling, over a 20-minute test cycle. Concurrently, the stirrer was run at 160 rpm and the viscosity of the solution calculated from measuring the current.

The test profile was as follows:

| Time | Type | Value |
| --- | --- | --- |
| 00:00:00 | Temp | 50° C. |
| 00:00:00 | Speed | 1000 rpm |
| 00:01:00 | Speed | 160 rpm |
| 00:01:00 | Temp | 50° C. |
| 00:04:30 | Temp | 90° C. |
| 00:09:30 | Temp | 90° C. |
| 00:15:00 | Temp | 30° C. |
| Idle temperature: 50° C. | | |
| End of test: 20 min | | |
| Time between readings: 4s | | |

Figure 3:
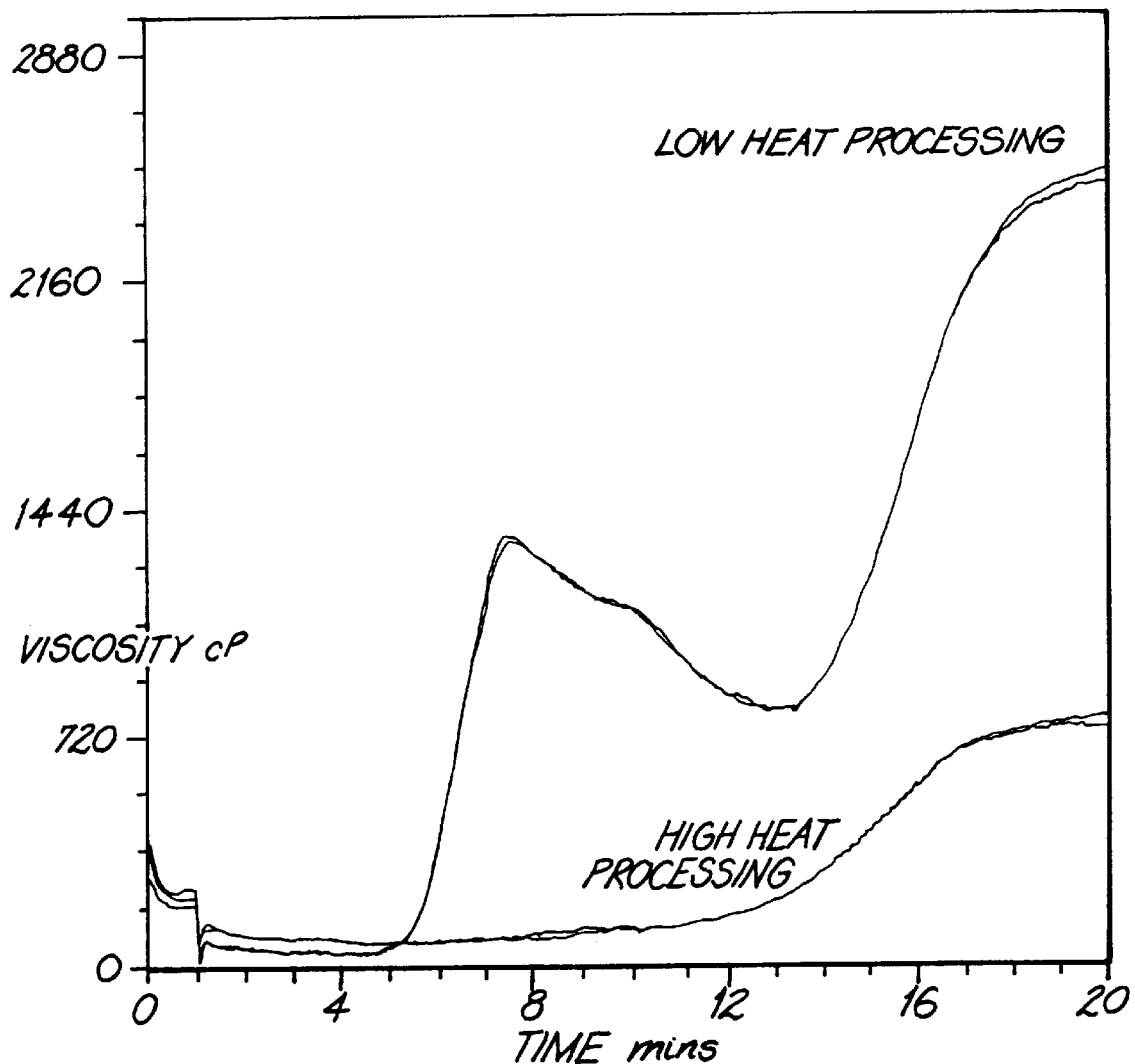
FIG. 3 is a sample result graph in which both temperature and viscosity readings of a skim milk powder sample are plotted against time.

FIG. 3 is a copy of the resultant plots of viscosity (left hand axis) against time, for samples of SMP which had undergone high- (112° C.) or low- (72° C.) heat processing. As the sample mixture of the low-heat processed SMP was heated to and held at around 90° C., the viscosity of the sample mixture rose and reached a first plateau. The viscosity rose and reached another plateau as the sample mixture was cooled. The sample which was processed at higher temperature for a longer time did not have a large peak during the heating cycle of the test. It is apparent that the test readily distinguishes the different processing histories of the two SMP samples.

The dual lines for viscosity for each SMP type indicate the test results for two different samples from the same source. It can be seen that the results were highly reproducible.

The above method may be adjusted to suit the particular type of dried milk product to be tested. For example, whey powder, which has a lower protein content but higher solids than WPC, may be tested at 3 g protein in 40 g sample solution with pH 6.5 buffer, spun at 320 rpm and heated to 90° C. in order to exaggerate denaturing of the proteins.

Another suitable preferred solvent system for use in the invention is dilute acid buffered to approximately pH 6.5.

While particular embodiments of this invention have been described, it will be evident to those skilled in the art that the present invention may be embodied in other specific forms without departing from the essential characteristics thereof. The present embodiments and examples therefore are to be considered in all respects as illustrative and not restrictive, the scope of the invention being indicated by the appended claims rather than by the foregoing description, and all changes which come within the meaning and range of equivalency of the claims therefore are intended to be embraced therein.

What is claimed is:

1. A method for determining the effect of the previous processing history on the functional properties of proteins in dried milk products, including the steps of taking a sample of the dried milk product, mixing said sample with a solvent and subjecting the mixture to conditions suitable for the milk proteins in said sample to enter solution, stirring said solution and assessing the viscosity of said solution; said viscosity providing an indicator of said processing history.

2. A method according to claim 1 wherein changes in viscosity of said solution over time are assessed and recorded.

3. A method according to claim 2 wherein said changes in viscosity are compared to known standards.

4. A method according to claim 1 wherein said solvent is water.

5. A method according to claim 1 wherein said solvent is dilute acid buffered to approximately pH 6.5.

6. A method according to claim 1 wherein said milk protein solution is heated to at least 60° C. while the viscosity is measured.

7. A method according to claim 1 wherein said dried milk product is whey protein concentrate.

8. A method according to claim 6 wherein the temperature of said milk protein solution is increased to approximately 80° C., held at that temperature and then decreased while the viscosity is measured.

9. A method according to claim 1 wherein said dried milk product is skim milk powder.

10. A method according to claim 6 wherein the temperature of said milk protein solution is increased to approximately 90° C., held at the temperature and then decreased while the viscosity is measured.

11. A method for determining the effect of previous processing history on the functional properties of proteins in dried milk products, including the steps of providing a sample container into which a sample mixture of a dried milk product and a solvent are placed, heat transfer means for controlled heating of said sample, stirring means positioned within said container and means for assessing and recording the temperature and the viscosity of the milk protein solution, and heating said sample mixture, stirring said mixture and assessing and recording the changes in said temperature and viscosity; said viscosity providing an indicator of said processing history.

12. A method of determining the previous processing history of a dried milk product, including the steps of providing a sample container into which a sample mixture of a dried milk product and a solvent are place, heat transfer means for controlled heating of said sample, stirring means positioned within said container and means for assessing and recording the temperature and the viscosity of the milk protein solution, and heating said sample mixture, stirring said mixture and assessing and recording the changes in said temperature and viscosity.

13. A method according to claim 12 for assessing the heat conditions under which said sample has been subjected during said processing history.

* * * * *